United States Patent [19]
McBride et al.

[11] Patent Number: 6,056,940
[45] Date of Patent: *May 2, 2000

[54] RADIOLABELED COMPOUNDS FOR THROMBUS IMAGING

[75] Inventors: William McBride, Summit, N.J.; Richard T. Dean; John Lister-James, both of Bedford, N.H.; Edward R. Civitello, Bradford, N.H.

[73] Assignee: Diatide, Inc., Londonderry, N.H.

[*] Notice: This patent is subject to a terminal disclaimer.

[21] Appl. No.: 08/535,170

[22] PCT Filed: Apr. 8, 1994

[86] PCT No.: PCT/US94/03878

§ 371 Date: Jan. 11, 1996

§ 102(e) Date: Jan. 11, 1996

[87] PCT Pub. No.: WO94/23758

PCT Pub. Date: Oct. 27, 1994

Related U.S. Application Data

[63] Continuation-in-part of application No. 08/439,905, May 12, 1995, Pat. No. 5,645,815, which is a continuation of application No. 08/044,825, Apr. 8, 1993, abandoned.

[51] Int. Cl.[7] .......................... A61K 51/00; A61M 36/14
[52] U.S. Cl. .................. 424/1.69; 424/1.11; 424/1.65; 424/9.1; 530/300; 530/324; 530/330; 530/326; 530/327; 530/325; 530/328; 530/529; 534/14
[58] Field of Search ........................ 424/1.11, 1.65, 424/1.69, 9.1; 530/300, 311, 317, 324–330, 333, 334, 338; 206/223, 569, 570; 534/7, 10–16

[56] References Cited

U.S. PATENT DOCUMENTS

| | | |
|---|---|---|
| 4,578,079 | 3/1986 | Ruoslahti et al. . |
| 4,792,525 | 12/1988 | Ruoslahti et al. . |
| 4,877,868 | 10/1989 | Reno et al. . |
| 4,952,562 | 8/1990 | Klein et al. . |
| 5,086,069 | 2/1992 | Klein et al. . |
| 5,225,181 | 7/1993 | Srivastava et al. ................. 424/1.11 |
| 5,443,816 | 8/1995 | Zamora et al. . |
| 5,645,815 | 7/1997 | Dean et al. ........................... 424/1.69 |
| 5,744,120 | 4/1998 | Edwards et al. ..................... 424/1.65 |

FOREIGN PATENT DOCUMENTS

| | | |
|---|---|---|
| 410537 | 1/1991 | European Pat. Off. . |
| 410539 | 1/1991 | European Pat. Off. . |
| 410540 | 1/1991 | European Pat. Off. . |
| 410541 | 1/1991 | European Pat. Off. . |
| 425212 | 2/1991 | European Pat. Off. . |
| 422938 | 4/1991 | European Pat. Off. . |
| 0453082 | 10/1991 | European Pat. Off. . |
| 422937 | 11/1991 | European Pat. Off. . |
| 422938 | 11/1991 | European Pat. Off. . |
| 0478328A1 | 1/1992 | European Pat. Off. . |
| 502536 | 3/1992 | European Pat. Off. . |
| 512829 | 5/1992 | European Pat. Off. . |
| 513810 | 5/1992 | European Pat. Off. . |
| WO 89/02752 | 4/1989 | WIPO . |
| WO 89/05150 | 6/1989 | WIPO . |
| 8910759 | 11/1989 | WIPO . |
| 9010463 | 9/1990 | WIPO . |
| 9015818 | 12/1990 | WIPO . |
| WO 90/15818 | 12/1990 | WIPO . |
| WO 91/01331 | 2/1991 | WIPO . |
| WO 91/15515 | 10/1991 | WIPO . |
| 9117173 | 11/1991 | WIPO . |
| WO 91/17173 | 11/1991 | WIPO . |
| 9213572 | 8/1992 | WIPO . |
| 9217492 | 10/1992 | WIPO . |
| WO 93/00095 | 1/1993 | WIPO . |
| WO 93/08174 | 4/1993 | WIPO . |
| 9321962 | 11/1993 | WIPO . |
| 9323085 | 11/1993 | WIPO . |
| 9325244 | 12/1993 | WIPO . |
| WO9422494 | 10/1994 | WIPO ........................... A61K 49/02 |

OTHER PUBLICATIONS

Baidoo et al (1990), Bioconjugate Chem., vol. 1, No. 2, pp. 132–137, Synthesis of Diaminedithiol Bifunctional Chetating Agents for Incorporation of Technetrium–99m into Biomolecules.

Bryson et al (1990), Inorg. Chem., vol. 29, No. 16, pp. 2948–2951, "Protecting Groups in the Preparation of Thiolate Complexes of Technetium".

Hartman, et al., (1992) "Non–Peptide Fibrinogen Receptor Antagonists. 1. Discovery and Design of Exosite Inhibitors" Journal of Medicinal Chemistry 35, 46404642.

Knight, et al., (1990) "Radiopharmaceuticals for Thrombus Detection" Seminars in Nuclear Medicine, XX, 52–67.

Ojima, et al., (1992) "Design and Synthesis of New RGD Peptides as Inhibitors of Human Platelet Aggregation" 204th Meeting, Amer. Chem. Soc. Abst. 44.

Plow, et al., (1985) "The effect of Arg–Gly–Asp–containing peptides on Fibrinogen and von Willebrand factor binding to platelets" Cell Biology 82, 8057–8061.

Rhodes, et al., (1986) "Technetium–99m Labeling of Murine Monoclonal Antibody Fragments" J. Nucl. Med. 27, 685–693.

*Primary Examiner*—Jose' G. Dees
*Assistant Examiner*—Dameron Jones
*Attorney, Agent, or Firm*—Patricia A. McDaniels; Kevin E. Noonan

[57] ABSTRACT

This invention relates to radiolabeled scintigraphic imaging agents, and methods and reagents for producing such agents. Specifically, the invention relates to specific binding compounds, including peptides, that bind to a platelet receptor that is the platelet GPIIb/IIIa receptor, methods and kits for making such compounds, and methods for using such compounds labeled with technetium-99m via a covalently-linked radiolabel-binding moiety to image thrombi in a mammalian body.

25 Claims, No Drawings

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
       (A) LENGTH: 8 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1..3
       (D) OTHER INFORMATION: /label= D-Tyr
           /note= "The tyrosine residue is in the D-stereo-
           chemical configuration"

(ix) FEATURE:
       (A) NAME/KEY: Modified-site
       (B) LOCATION: 1..3
       (D) OTHER INFORMATION: /label= Apc
           /note= "Residue Xaa = L(S-3 aminopropyl)
           cysteine."

(ix) FEATURE:
       (A) NAME/KEY: Modified-site
       (B) LOCATION: 1..5
       (D) OTHER INFORMATION: /label= Cyclic
           /note= "The sidechain sulfur of the Cys
           residue is covalently linked to the amino
           terminus by a -CH2CO- group."

(xi) SEQUENCE DESCRIPTION: SEQ ID NO:1:

Tyr Xaa Gly Asp Cys Gly Gly Gly
1               5

(2) INFORMATION FOR SEQ ID NO:2:

(i) SEQUENCE CHARACTERISTICS:
       (A) LENGTH: 7 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1..3
       (D) OTHER INFORMATION: /label= D-Tyr
           /note= "The tyrosine residue is in the D-stereo-
           chemical configuration"

(ix) FEATURE:
       (A) NAME/KEY: Modified-site
       (B) LOCATION: 1..3
       (D) OTHER INFORMATION: /label= Apc
           /note= "Residue Xaa = L(S-3 aminopropyl)
           cysteine."

(ix) FEATURE:
       (A) NAME/KEY: Modified-site
       (B) LOCATION: 1..5
       (D) OTHER INFORMATION: /label= Cyclic
           /note= "The sidechain sulfur of the Cys
           residue is covalently linked to the amino
           terminus by a -CH2CO- group."

(xi) SEQUENCE DESCRIPTION: SEQ ID NO:2:

Tyr Xaa Gly Asp Cys Lys Gly

```
1               5
```

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= D-Tyr
            /note= "The tyrosine residue is in the D-stereo-
            chemical configuration"

(ix) FEATURE:
        (A) NAME/KEY: Modified-site
        (B) LOCATION: 1..3
        (D) OTHER INFORMATION: /label= Apc
            /note= "Residue Xaa = L(S-3 aminopropyl)
            cysteine."

(ix) FEATURE:
        (A) NAME/KEY: Modified-site
        (B) LOCATION: 1..5
        (D) OTHER INFORMATION: /label= Cyclic
            /note= "The sidechain sulfur of the Cys
            residue is covalently linked to the amino
            terminus by a -CH2CO- group."

(xi) SEQUENCE DESCRIPTION: SEQ ID NO:3:

```
Tyr Xaa Gly Asp Cys Gly Gly
1               5
```

(2) INFORMATION FOR SEQ ID NO:4:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= D-Tyr
            /note= "The tyrosine residue is in the D-stereo-
            chemical configuration"

(ix) FEATURE:
        (A) NAME/KEY: Modified-site
        (B) LOCATION: 1..3
        (D) OTHER INFORMATION: /label= Apc
            /note= "Residue Xaa = L(S-3 aminopropyl)
            cysteine."

(ix) FEATURE:
        (A) NAME/KEY: Modified-site
        (B) LOCATION: 1..5
        (D) OTHER INFORMATION: /label= Cyclic
            /note= "The sidechain sulfur of the Cys
            residue is covalently linked to the amino
            terminus by a -CH2CO- group."

(xi) SEQUENCE DESCRIPTION: SEQ ID NO:4:

```
Tyr Xaa Gly Asp Cys
1               5
```

(2) INFORMATION FOR SEQ ID NO:5:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1..3
            (D) OTHER INFORMATION: /label= D-Tyr
                /note= "The tyrosine residue is in the D-stereo-
                chemical configuration"

(ix) FEATURE:
            (A) NAME/KEY: Modified-site
            (B) LOCATION: 1..3
            (D) OTHER INFORMATION: /label= Apc
                /note= "Residue Xaa = L(S-3 aminopropyl)
                cysteine."

(ix) FEATURE:
            (A) NAME/KEY: Modified-site
            (B) LOCATION: 1..5
            (D) OTHER INFORMATION: /label= Cyclic
                /note= "The sidechain sulfur of the Cys
                residue is covalently linked to the amino
                terminus by a -CH2CO- group."

(xi) SEQUENCE DESCRIPTION: SEQ ID NO:5:

Tyr Xaa Gly Asp Cys Lys
1               5

(2) INFORMATION FOR SEQ ID NO:6:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1..3
            (D) OTHER INFORMATION: /label= D-Tyr
                /note= "The tyrosine residue is in the D-stereo-
                chemical configuration"

(ix) FEATURE:
            (A) NAME/KEY: Modified-site
            (B) LOCATION: 1..3
            (D) OTHER INFORMATION: /label= Amp
                /note= "Residue Xaa = 4-amidinophenylalanine."

(ix) FEATURE:
            (A) NAME/KEY: Modified-site
            (B) LOCATION: 1..5
            (D) OTHER INFORMATION: /label= Cyclic
                /note= "The sidechain sulfur of the Cys
                residue is covalently linked to the amino
                terminus by a -CH2CO- group."

(xi) SEQUENCE DESCRIPTION: SEQ ID NO:6:

Tyr Xaa Gly Asp Cys
1               5

(2) INFORMATION FOR SEQ ID NO:7:

(i) SEQUENCE CHARACTERISTICS:
            (A) LENGTH: 6 amino acids
            (B) TYPE: amino acid
            (D) TOPOLOGY: linear (ii) MOLECULE TYPE: peptide

```
    (ix) FEATURE:
         (A) NAME/KEY: Modified-site
         (B) LOCATION: 1..3
         (D) OTHER INFORMATION: /label= D-Tyr
             /note= "The tyrosine residue is in the D-stereo-
             chemical configuration"

(ix) FEATURE:
         (A) NAME/KEY: Modified-site
         (B) LOCATION: 1..3
         (D) OTHER INFORMATION: /label= Amp
             /note= "Residue Xaa = 4-amidinophenylalanine."

(ix) FEATURE:
         (A) NAME/KEY: Modified-site
         (B) LOCATION: 1..5
         (D) OTHER INFORMATION: /label= Cyclic
             /note= "The sidechain sulfur of the Cys
             residue is covalently linked to the amino
             terminus by a -CH2CO- group."

(xi) SEQUENCE DESCRIPTION: SEQ ID NO:7:

Tyr Xaa Gly Asp Cys Lys
1               5

(2) INFORMATION FOR SEQ ID NO:8:

(i) SEQUENCE CHARACTERISTICS:
         (A) LENGTH: 8 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /label= D-Tyr
             /note= "The tyrosine residue is in the D-stereo-
             chemical configuration"

(ix) FEATURE:
         (A) NAME/KEY: Modified-site
         (B) LOCATION: 1..5
         (D) OTHER INFORMATION: /label= Cyclic
             /note= "The sidechain sulfur of the Cys
             residue is covalently linked to the amino
             terminus by a -CH2CO- group."

(ix) FEATURE:
         (A) NAME/KEY: Modified-site
         (B) LOCATION: 6..8
         (D) OTHER INFORMATION: /label= Tc-99m-chelator
             /note= "The sidechain sulfur atoms of both Cys
             residues are each protected with an
             acetamidomethyl group"

(ix) FEATURE:
         (A) NAME/KEY: Modified-site
         (B) LOCATION: 8
         (D) OTHER INFORMATION: /label= Amide
             /note= "The carboxyl terminus is modified to an
             amide"

(xi) SEQUENCE DESCRIPTION: SEQ ID NO:8:

Tyr Arg Gly Asp Cys Cys Gly Cys
1               5

(2) INFORMATION FOR SEQ ID NO:9:

(i) SEQUENCE CHARACTERISTICS:
         (A) LENGTH: 10 amino acids
         (B) TYPE: amino acid
         (D) TOPOLOGY: linear
```

```
    (ii) MOLECULE TYPE: peptide (ix) FEATURE:
         (A) NAME/KEY: Modified-site
         (B) LOCATION: 1
         (D) OTHER INFORMATION: /label= D-Tyr
             /note= "The tyrosine residue is in the D-stereo-
             chemical configuration"

(ix) FEATURE:
         (A) NAME/KEY: Modified-site
         (B) LOCATION: 1..5
         (D) OTHER INFORMATION: /label= Cyclic
             /note= "The sidechain sulfur of the Cys
             residue is covalently linked to the amino
             terminus by a -CH2CO- group."

(ix) FEATURE:
         (A) NAME/KEY: Modified-site
         (B) LOCATION: 8..10
         (D) OTHER INFORMATION: /label= Tc-99m-chelator
             /note= "The sidechain sulfur atoms of both Cys
             residues are each protected with an
             acetamidomethyl group"

(ix) FEATURE:
         (A) NAME/KEY: Modified-site
         (B) LOCATION: 10
         (D) OTHER INFORMATION: /label= Amide
             /note= "The carboxyl terminus is modified to an
             amide"

(xi) SEQUENCE DESCRIPTION: SEQ ID NO:9:

Tyr Arg Gly Asp Cys Gly Gly Cys Gly Cys
1               5                   10

(2) INFORMATION FOR SEQ ID NO:10:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /label= D-Tyr
             /note= "The tyrosine residue is in the D-stereo-
             chemical configuration"

(ix) FEATURE:
         (A) NAME/KEY: Modified-site
         (B) LOCATION: 2
         (D) OTHER INFORMATION: /label= Apc
             /note= "Residue Xaa = L(S-3 aminopropyl)
             cysteine."

(ix) FEATURE:
         (A) NAME/KEY: Modified-site
         (B) LOCATION: 1..5
         (D) OTHER INFORMATION: /label= Cyclic
             /note= "The sidechain sulfur of the Cys
             residue is covalently linked to the amino
             terminus by a -CH2CO- group."

(ix) FEATURE:
         (A) NAME/KEY: Modified-site
         (B) LOCATION: 9..11
         (D) OTHER INFORMATION: /label= Tc-99m-chelator
             /note= "The sidechain sulfur atoms of both Cys
             residues are each protected with an
             acetamidomethyl group"

(ix) FEATURE:
```

(A) NAME/KEY: Modified-site
            (B) LOCATION: 11
            (D) OTHER INFORMATION: /label= Amide
                /note= "The carboxyl terminus is modified to an
                amide"

(xi) SEQUENCE DESCRIPTION: SEQ ID NO:10:

Tyr Xaa Gly Asp Cys Gly Gly Gly Cys Gly Cys
1               5                   10

(2) INFORMATION FOR SEQ ID NO:11:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 11..13
        (D) OTHER INFORMATION: /label= Tc-99m-chelator
            /note= "The sidechain sulfur atoms of both Cys
            residues are each protected with an
            acetamidomethyl group"

(ix) FEATURE:
        (A) NAME/KEY: Modified-site
        (B) LOCATION: 13
        (D) OTHER INFORMATION: /label= Amide
            /note= "The carboxyl terminus is modified to an
            amide"

(xi) SEQUENCE DESCRIPTION: SEQ ID NO:11:

Gly Arg Gly Asp Val Arg Gly Asp Phe Lys Cys Gly Cys
1               5                   10

(2) INFORMATION FOR SEQ ID NO:12:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 10..12
        (D) OTHER INFORMATION: /label= Tc-99m-chelator
            /note= "The sidechain sulfur atoms of both Cys
            residues are each protected with an
            acetamidomethyl group"

(ix) FEATURE:
        (A) NAME/KEY: Modified-site
        (B) LOCATION: 12
        (D) OTHER INFORMATION: /label= Amide
            /note= "The carboxyl terminus is modified to an
            amide"

(xi) SEQUENCE DESCRIPTION: SEQ ID NO:12:

Gly Arg Gly Asp Val Arg Gly Asp Phe Cys Gly Cys
1               5                   10

(2) INFORMATION FOR SEQ ID NO:13:

(i) SEQUENCE CHARACTERISTICS:
        (A) LENGTH: 17 amino acids
        (B) TYPE: amino acid
        (D) TOPOLOGY: linear

```
    (ii) MOLECULE TYPE: peptide (ix) FEATURE:
         (A) NAME/KEY: Modified-site
         (B) LOCATION: 1
         (D) OTHER INFORMATION: /label= D-Tyr
             /note= "The tyrosine residue is in the D-stereo-
             chemical configuration"

(ix) FEATURE:
         (A) NAME/KEY: Modified-site
         (B) LOCATION: 2
         (D) OTHER INFORMATION: /label= Apc
             /note= "Residue Xaa = L(S-3 aminopropyl)
             cysteine."

(ix) FEATURE:
         (A) NAME/KEY: Modified-site
         (B) LOCATION: 1..5
         (D) OTHER INFORMATION: /label= Cyclic
             /note= "The sidechain sulfur of the Cys
             residue is covalently linked to the amino
             terminus by a -CH2CO- group."

(ix) FEATURE:
         (A) NAME/KEY: Modified-site
         (B) LOCATION: 8..10
         (D) OTHER INFORMATION: /label= Tc-99m-chelator
             /note= "The sidechain sulfur atoms of both Cys
             residues are each protected with an
             acetamidomethyl group"

(ix) FEATURE:
         (A) NAME/KEY: Modified-site
         (B) LOCATION: 13
         (D) OTHER INFORMATION: /label= D-Phe
             /note= "The phenylalanine residue is in the D-stereo-
             chemical configuration"

(ix) FEATURE:
         (A) NAME/KEY: Modified-site
         (B) LOCATION: 17
         (D) OTHER INFORMATION: /label= Amide
             /note= "The carboxyl terminus is modified to an
             amide"

(xi) SEQUENCE DESCRIPTION: SEQ ID NO:13:

Tyr Xaa Gly Asp Cys Gly Gly Cys Gly Cys Gly Gly Phe Pro Arg Pro Gly
1               5                   10                  15

(2) INFORMATION FOR SEQ ID NO:14:

(i) SEQUENCE CHARACTERISTICS:
         (A) LENGTH: 15 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1..3
         (D) OTHER INFORMATION: /label= Tc-99m-chelator
             /note= "The sidechain sulfur atoms of both Cys
             residues are each protected with an
             acetamidomethyl group"

(ix) FEATURE:
         (A) NAME/KEY: Modified-site
         (B) LOCATION: 15
         (D) OTHER INFORMATION: /label= Amide
             /note= "The carboxyl terminus is modified to an
             amide"

(xi) SEQUENCE DESCRIPTION: SEQ ID NO:14:

Cys Gly Cys Arg Arg Arg Arg Arg Arg Arg Arg Arg Gly Asp Val
```

-continued

```
1               5              10             15
```

(2) INFORMATION FOR SEQ ID NO:15:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Acetyl
            /note= "The amino terminus is modified with an
            acetyl group."

(ix) FEATURE:
        (A) NAME/KEY: Modified-site
        (B) LOCATION: 13..15
        (D) OTHER INFORMATION: /label= Tc-99m-chelator
            /note= "The sidechain sulfur atoms of both Cys
            residues are each protected with an
            acetamidomethyl group"

(xi) SEQUENCE DESCRIPTION: SEQ ID NO:15:

```
Ser Tyr Gly Arg Gly Asp Val Arg Gly Asp Phe Lys Cys Gly Cys
1               5                  10                  15
```

(2) INFORMATION FOR SEQ ID NO:16:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Acetyl
            /note= "The amino terminus is modified with an
            acetyl group."

(xi) SEQUENCE DESCRIPTION: SEQ ID NO:16:

```
Ser Tyr Gly Arg Gly Asp Val Arg Gly Asp Phe Lys Cys Thr Cys Cys Ala
1               5                  10                  15
```

RADIOLABELED COMPOUNDS FOR THROMBUS IMAGING

This application is a 371 of PCT/US94/03878, filed April 8, 1994, which claims priority to U.S. patent application Ser. No. 08/044,825, filed Apr. 8, 1993 and now abandoned; this application is also a continuation-in-part of U.S. patent application Ser. No. 08/439,905, filed May 12, 1995 and now U.S. Pat. No. 5,645,815; which is a continuation of U.S. patent application Ser. No. 08/044,825, filed Apr. 8, 1993 and now abandoned.

BACKGROUND OF THE INVENTION

1. Field of the Invention

This invention relates to scintigraphic imaging agents and reagents, and methods for producing such agents and reagents. Specifically, the invention relates to reagents that can be radiolabeled with technetium-99m (Tc-99m), methods and kits for making and radiolabeling such reagents, and methods for using such radiolabeled reagents to image sites of thrombus formation in a mammalian body.

2. Description of the Prior Art

Thrombosis and thromboembolism, in particular deep vein thrombosis (DVT) and pulmonary embolism (PE), are common clinical conditions that are associated with significant morbidity and mortality. It has been estimated that in the U.S. approximately 5 million patients experience one or more episodes of DVT per year and that over 500,000 cases of pulmonary embolism occur, resulting in 100,000 deaths (J. Seabold, Society of Nuclear Medicine Annual Meeting 1990). It has also been estimated that over 90% of all pulmonary emboli arise from DVT in the lower extremities. Anticoagulant therapy can effectively treat these conditions if applied early enough. However, such treatment is associated with risks (e.g. internal bleeding) that prevent unnecessary prophylactic application. More advanced techniques of thrombolytic intervention (such as the administration of recombinant tissue plasminogen activator or streptokinase) can be used in acute cases, but these techniques carry even greater risk. Moreover, effective clinical application of these techniques requires that the site of the offending thrombus be identified so as to monitor the effect of treatment.

For these reasons, a rapid means of localizing thrombi in vivo, most preferably using non-invasive methods, is highly desirable. Methods currently utilized for the identification of sites of deep-vein thrombosis are contrast venography and compression B-mode ultrasound; the choice of which technique is used depends on the expected location of the thrombus. However, the former technique is invasive and both techniques are uncomfortable for the patient. In addition, these methods are in many cases either unsuitable or yield inaccurate results.

Current methods used to diagnose PE include chest X-ray, electrocardiogram (EKG), areterial oxygen tension, perfusion and ventilation lung scans, and pulmonary angiography. Apart from the latter (invasive) procedure, none of these methods is capable of providing an unequivocal diagnosis.

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

A variety of radionuclides are known to be useful for radioimaging, including $^{67}$Ga, $^{68}$Ga, $^{99m}$Tc (Tc-99m), $^{111}$In, $^{123}$I, $^{125}$I, $^{169}$Yb and $^{186}$Re. Of these radionuclides, Tc-99m and $^{111}$In are preferred single photon-emitting radionuclides and $^{68}$Ga is preferred as a positron-emitting radionuclide. Tc-99m is a preferred radionuclide because it emits gamma radiation at 140 keV, it has a physical half-life of 6 hours, and it is readily available on-site using a molybdenum-99/technetium-99m generator.

A gamma-emitting radiotracer that binds specifically to a component of a thrombus in preference to other tissues when administered in vivo can provide an external scintigraphic image which defines the location of the thrombus-bound radiotracer and hence the thrombus. Thrombi are constructs of blood cells, largely activated platelets, enmeshed in cross-linked fibrin. Activated platelets are particularly good targets for radioimaging thrombi because they are not normally found in circulating blood (which contains unactivated platelets).

Activated platelets express the GPIIb/IIIa receptor on their cell surfaces. The normal ligand for this receptor is fibrinogen (Plow et al., 1987, *Perspectives in Inflammation, Neoplasia and Vascular Cell Biology*, pp. 267–275). However, small, synthetic analogues, which may be but are not necessarily peptides, have been developed that bind to this receptor (examples include Klein et al., 1992, U.S. Pat. No. 5,086,069 and Egbertson et al., 1992, European Patent Application No. EPA 0478328A1). Although many of these synthetic molecules bind with only low affinity, others have been made that have very high affinity (see Egbertson et al., ibid.). This invention provides small, synthetic, radiolabeled (preferably Tc-99m, $^{111}$In or 68Ga labeled) compounds that bind to the GPIIb/IIIa receptor with high affinity, as scintigraphic agents for non-invasive imaging of thrombi in vivo.

Attempts to provide radiotracers for imaging thrombi are known in the prior art. These include autologous platelets, labeled with either $^{111}$In or $^{99m}$Tc (Tc-99m), and 123I- and 125I-labeled fibrinogen (the latter detected with a gamma scintillation probe as opposed to a gamma camera). Additional radiolabeled compounds used to label thrombi include plasmin, plasminogen activators, heparin, fibronectin, fibrin Fragment $E_1$ and anti-fibrin and anti-platelet monoclonal antibodies [see Knight, 1990, Sem. Nucl. Med. 20: 52–67 for review].

Compounds having the ability to bind to the platelet GPIIb/IIIa receptor are known in the prior art.

Ruoslahti & Pierschbacher, U.S. Pat. No. 4,578,079 describe peptides of sequence X-Arg-Gly-Asp-R-Y, wherein X and Y are either H or an amino acid, and R is Thr or Cys, the peptides being capable of binding to platelets.

Ruoslahti & Pierschbacher, U.S. Pat. No. 4,792,525 describe peptides of sequence Arg-Gly-Asp-X, wherein X is Ser, Thr or Cys, the peptides being capable of binding to platelets.

Klein et al., 1992, U.S. Pat. No. 5,086,069 disclose guanine derivatives that bind to the GPIIb/IIIa receptor.

Pierschbacher et al., 1989, PCT/US88/04403 disclose conformationally-restricted RGD containing peptides for inhibiting cell attachment to a substratum.

Nutt et al., 1990, European Patent Application 90202015.5 disclose cyclic RGD peptides that are fibrinogen receptor antagonists.

Nutt et al., 1990, European Patent Application 90202030.4 disclose cyclic RGD peptides that are fibrinogen receptor antagonists.

Nutt et al., 1990, European Patent Application 90202031.2 disclose cyclic RGD peptides that are fibrinogen receptor antagonists.

Nutt et al., 1990, European Patent Application 90202032.0 disclose cyclic RGD peptides that are fibrinogen receptor antagonists.

Nutt et al., 1990, European Patent Application 90311148.2 disclose cyclic peptides that are fibrinogen receptor antagonists.

Nutt et al., 1990, European Patent Application 90311151.6 disclose cyclic peptides that are fibrinogen receptor antagonists.

Ali et al., 1990, European Patent Application 90311537.6 disclose cyclic peptides that are fibrinogen receptor antagonists.

Barker et al., 1991, PCT/US90/03788 disclose cyclic peptides for inhibiting platelet aggregation.

Pierschbacher et al., 1991, PCT/US91102356 disclose cyclic peptides that are fibrinogen receptor antagonists.

Duggan et al, 1992, European Patent Application 92304111.5 disclose fibrinogen receptor antagonists.

Garland et al, 1992 European Patent Applications 92103861.8 and 92108214.5 disclose phenylamide derivatives as platelet aggregation inhibitors.

Bondinell et al, 1993, International Patent Application Serial No. PCT/US92/05463 disclose bicyclic fibrinogen antagonists.

Blackburn et al., International Patent Application Serial No. PCT/US92/08788, disclose nonpeptidyl integrin inhibitors having specificity for the GPIIb/IIIa receptor.

Egbertson et al., 1992, European Patent Application 0478328A1 disclose tyrosine derivatives that bind with high affinity to the GPIIb/IIIa receptor.

Ojima et al., 1992, 204th Meeting, Amer. Chem. Soc. Abst. 44 disclose synthetic multimeric RDGF peptides useful in inhibiting platelet aggregation.

Hartman et al., 1992, J. Med. Chem. 35: 4640–4642 describe tyrosine derivatives that have a high affinity for the GPIIb/IIIa receptor.

Radiolabeled peptides for radioimaging thrombi have been reported in the prior art.

Stuttle, 1990, PCT/GB90100933 discloses radioactively labeled peptides containing from 3 to 10 amino acids comprising the sequence arginine-glycine-aspartic acid (RGD), capable of binding to an RGD binding site in vivo.

Rodwell et al., 1991, PCT/US91/03116 disclose conjugates of "molecular recognition units" with "effector domains".

The use of chelating agents for radiolabeling peptides, and methods for labeling peptides with Tc-99m are known in the prior art and are disclosed in co-pending U.S. patent applications Ser. No. 07/653,012, now abandoned, a continuation of which issued as U.S. Pat. No. 5,811,394; Ser. No. 07/807,062, now U.S. Pat. No. 5,443,815; Ser. No. 07/871,282, a divisional of which issued as U.S. Pat. No. 5,780,007; Ser. No. 07/886,752, now abandoned, a continuation of which issued as U.S. Pat. No. 5,849,260; Ser. No. 07/893,981, now U.S. Pat. No. 5,508,020; Ser. No. 07/955,466, now abandoned; Ser. No. 08/019,864, now U.S. Pat. No. 5,552,525; and Ser. No. 08/073,577, now U.S. Pat. No. 5,561,220, and radiolabeled peptides for use as scintigraphic imaging agents for imaging thrombi are known in the prior art and are disclosed in co-pending U.S. patent applications Ser. No. 07/886,752, now abandoned, a continuation of which issued as U.S. Pat. No. 5,849,260; Ser. No. 07/893, 981, now U.S. Pat. No. 5,508,020; and Ser. No. 08/044,825, now abandoned, a continuation of which issued as U.S. Pat. No. 5,645,815, which are hereby incorporated by reference.

There remains a need for small (to enhance blood and background tissue clearance), synthetic (to make routine manufacture practicable and to ease regulatory acceptance), high-affinity, specific-binding molecules radiolabeled with a convenient radiolabel, preferably Tc-99m, for use in imaging thrombi in vivo. Small synthetic compounds that bind specifically to the GPIIb/IIIa receptor on activated platelets, that are radiolabeled with a convenient radioisotope, preferably Tc-99m, $^{111}$In or $^{68}$Ga, fulfill this need in the art, and are provided by this invention.

SUMMARY OF THE INVENTION

The present invention provides scintigraphic thrombus imaging agents that are radioactively-labeled reagents. Specifically, the invention provides reagents for preparing thrombus imaging agents that are radiolabeled with technetium-99m (Tc-99m), $^{111}$In or $^{68}$Ga, preferably with Tc-99m. The reagents of the invention are each comprised of a specific binding compound, including but not limited to peptides, that binds specifically and with high affinity to the platelet glycoprotein IIb/IIIa (GPIIb/IIIa) receptor, that is covalently linked to a radiolabel-complexing moiety.

For optimal imaging, the reagent must be capable of binding to the platelet GPIIb/IIIa receptor with sufficient affinity that it inhibits the adenosine diphosphate (ADP)-induced aggregation of human platelets in a standard platelet aggregation assay (see Example 3 below) when present at a concentration of no more than 0.3 $\mu$M. Also, it is of distinct commercial advantage to use small compounds, preferably having a molecular weight of less than about 10,000 daltons. Such small compounds can be readily manufactured. Moreover, they are likely not to be immunogenic and to clear rapidly from the vasculature, thus allowing for better and more rapid imaging of thrombi. In contrast, larger molecules such as antibodies of fragments thereof, or other biologically-derived peptides larger than 10,000 daltons, are costly to manufacture, and are likely to be immunogenic and clear more slowly from the bloodstream, thereby interfering with rapid diagnoses of thrombi in vivo.

The invention also provides reagents wherein the specific binding compounds are linear or cyclic peptides having an amino acid sequence of 4 to 100 amino acids.

One aspect of the invention provides a reagent for preparing a thrombus imaging agent that is capable of being radiolabeled for imaging thrombi within a mammalian body, comprising a specific binding compound that specifically binds to the platelet GPIIb/IIIa receptor, and that is covalently linked to a Tc-99m complexing moiety of formula:

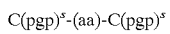
                    I.

wherein $C(pgp)^s$ is a protected cysteine and (aa) is any primary $\alpha$- or $\beta$-amino acid not containing a thiol group. In a preferred embodiment, the amino acid is glycine.

In another embodiment, the invention provides a reagent for preparing a thrombus imaging agent that is capable of being radiolabeled for imaging thrombi within a mammalian body, comprising a specific binding compound that specifically binds to the platelet GPIIb/IIIa receptor, that is covalently linked to a Tc-99m complexing moiety comprising a single thiol-containing moiety of formula:

                    II.

wherein A is H, HOOC, $H_2NOC$, (amino acid or peptide)-NHOC, (amino acid or peptide)-OOC or $R^4$; Z is H or $R^4$ B is H, SH or —NHR³, —N(R³), —N(R)-(amino acid or peptide) or R⁴; X is SH or —NHR³, N(R³)-(amino acid or peptide) or R⁴; R¹, R², R³ and R⁴ are independently H or straight or branched chain or cyclic lower alkyl; n is 0, 1 or 2; and: (1) where B is —NHR³ or —N(R³)-(amino acid or peptide), X is SH and n is 1 or 2; (2) where X is —NHR or —N(R³)-(amino acid or peptide), B is SH and n is 1 or 2; (3) where B is H or R⁴, A is HOOC, H₂NOC, (amino acid or peptide)-NHOC, (amino acid or peptide)-OOC, X is SH and n is 0 or 1; (4) where A is H or R⁴, then where B is SH, X is —NHR³ or —N(R³)-(amino acid or peptide) and where X is SH, B is —NHR³ or —N(R³)-(amino acid or peptide); (5) where X is H or R⁴, A is HOOC, H₂NOC, (amino acid or peptide)-NHOC, (amino acid or peptide)-OOC and B is SH; (6) where Z is methyl, X is methyl, A is HOOC, H₂NOC, (amino acid or peptide)-NHOC, (amino acid or peptide)-OOC and B is SH and n is 0; and B; and wherein the thiol moiety is in the reduced form and wherein (amino acid) is any primary α- or β-amino acid not containing a thiol group.

In particular embodiments of this aspect of the invention, the radiolabel-complexing moiety has a formula that is:

IIa. -(amino acid)¹-(amino acid)²-{A-CZ(B)-[C(R¹R²)]ₙ-X},

IIb. -{A-CZ(B)-[C(R¹R²)]ₙ-X}-(amino acid)¹-(amino acid)²,

IIc. -(a primary α,ω- or β,ω-diamino acid)-(amino acid)¹-{A-CZ(B)-[C(R¹R²)]ₙ-X}, or IId. -{A-CZ(B)-[C(R¹R²)]ₙ-X}-(amino acid)¹-(a primary α,β- or α,γ-diamino acid)

wherein (amino acid)¹ and (amino acid)² are each independently any naturally-ocurring, modified, substituted or altered α- or β-amino acid not containing a thiol group; A is H, HOOC, H₂NOC, (amino acid or peptide)-NHOC, (amino acid or peptide)-OOC or R⁴; Z is H or R⁴ B is H, SH or —NHR³, —N(R³)-(amino acid or peptide) or R⁴; X is SH or —NHR³, —N(R³)-(amino acid or peptide) or R⁴; R¹, R², R³ and R⁴ are independently H or straight or branched chain or cyclic lower alkyl; n is an integer that is either 0, 1 or 2; and: (1) where B is —NHR³ or —N(R³)-(amino acid or peptide), X is SH and n is 1 or 2; (2) where X is —NHR³ or —N(R³)-(amino acid or peptide), B is SH and n is 1 or 2; (3) where B is H or R⁴, A is HOOC, H₂NOC, (amino acid or peptide)-NHOC, (amino acid or peptide)-OOC, X is SH and n is 0 or 1; (4) where A is H or R⁴, then where B is SH, X is —NHR³ or —N(R³)-(amino acid or peptide) and where X is SH, B is —NHR³ or —N(R³)-(amino acid or peptide); (5) where X is H or R⁴, A is HOOC, H₂NOC, (amino acid or peptide)-NHOC, (amino acid or peptide)-OOC and B is SH; (6) where Z is methyl, X is methyl, A is HOOC, H₂NOC, (amino acid or peptide)-NHOC, (amino acid or peptide)-OOC and B is SH and n is 0; and (7) where B is SH and X is SH, n is not 0; and wherein the thiol group is in the reduced form.

In another embodiment, the invention provides a reagent for preparing a thrombus imaging agent that is capable of being radiolabeled for imaging thrombi within a mammalian body, comprising a specific binding compound that specifically binds to the platelet GPIIb/IIIa receptor, and that is covalently linked to a radiolabel-complexing moiety of formula:

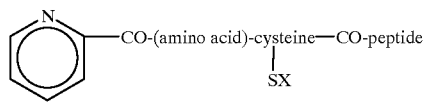

III.

[for purposes of this invention, radiolabel-binding moieties having this structure will be referred to as picolinic acid (Pic)-based moieties];

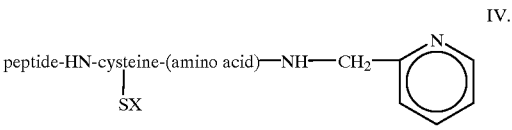

IV.

[for purposes of this invention, radiolabel-binding moieties having this structure will be referred to as picolylanine (Pica)-based moieties]; wherein X is H or a protecting group; (amino acid) is any primary α- or β-amino acid not containing a thiol group; the radiolabel-complexing moiety is covalently lined to the peptide and the complex of the radiolabel-complexing moiety and the radiolabel is electrically neutral. In a preferred embodiment, the amino acid is glycine and X is an acetamidomethyl protecting group. In additional preferred embodiments, the peptide is covalently linked to the radiolabel-complexing moiety via an amino acid, most preferably glycine.

Yet another embodiment of the invention provides a reagent for preparing a thrombus imaging agent that is capable of being radiolabeled for imaging thrombi within a mammalian body, comprising a specific binding compound that specifically binds to the platelet GPIIb/IIIa receptor, and that is covalently linked to a radiolabel-complexing moiety that is a bisamino bisthiol radiolabel-complexing moiety. The bisamino bisthiol moiety in this embodiment of the invention has a formula selected from the group consisting of:

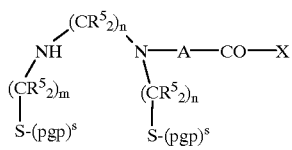

V.

wherein each R⁵ can be independently H, CH₃ or C₂H₅; each (pgp)ˢ can be independently a thiol protecting group or H; m, n and p are independently 2 or 3; A is linear or cyclic lower alkyl, aryl, heterocyclyl, combinations or substituted derivatives thereof; and X is peptide; and

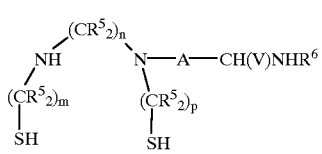

VI.

wherein each R⁵ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or CO-(amino acid or peptide); $R^6$ is H, (amino acid) or peptide; provided that when V is H, $R^6$ is amino acid or peptide and when $R^6$ is H, V is amino acid or peptide, wherein (amino acid) is any primary α- or β-amino acid not containing a thiol group. [For purposes of this invention, radiolabel-binding moieties having these structures will be referred to as "BAT" moieties]. In a preferred embodiment, the peptide is covalently linked to the radiolabel-complexing moiety via an amino acid, most preferably glycine.

In preferred embodiments of the aforementioned aspects of this invention, the specific binding compound is a peptide comprised of between 4 and 100 amino acids. The most preferred embodiment of the radiolabel is technetium-99m.

The reagents of the invention may be formed wherein the specific binding compounds or the radiolabel-complexing moieties are covalently linked to a polyvalent linking moiety. Polyvalent linking moieties of the invention are comprised of at least 2 identical linker functional groups capable of covalently bonding to specific binding compounds or radiolabel-complexing moieties. Preferred linker functional groups are primary or secondary amines, hydroxyl groups, carboxylic acid groups or thiol-reactive groups. In preferred embodiments, the polyvalent linking moieties are comprised of bis-succinimidylmethylether (BSME), 4-(2,2-dimethylacetyl)benzoic acid (DMAB), tris(succinimidylethyl)amine (TSEA), tris(2-chloroacetamidoethyl)amine, 1,2-bis-[2-(chloroacetamido)ethoxy]ethane, and N-[2-(N',N'-bis(2-succinimidoethyl)aminoethyl)]-$N^6$,$N^9$-bis(2-methyl-2-mercaptopropyl)-6,9-diazonanamide (BAT-BS).

The invention also comprises scintigraphic imaging agents that are complexes of the reagents of the invention with Tc-99m, $^{111}$In or $^{68}$Ga, most preferably Tc-99m and methods for radiolabeling the reagents. Tc-99m radiolabeled complexes provided by the invention are formed by reacting the reagents of the invention with Tc-99m in the presence of a reducing agent. Preferred reducing agents include but are not limited to dithionite ion, stannous ion and ferrous ion. Complexes of the invention are also formed by labeling the reagents of the invention with Tc-99m by ligand exchange of a prereduced Tc-99m complex as provided herein.

The invention also provides kits for preparing scintigraphic imaging agents that are the reagents of the invention radiolabeled with Tc-99m. Kits for labeling the reagents provided by the invention with Tc-99m are comprised of a sealed vial containing a predetermined quantity of a reagent of the invention and a sufficient amount of reducing agent to label the reagent with Tc-99m.

This invention provides methods for preparing peptide reagents of the invention by chemical synthesis in vitro. In a preferred embodiment, peptides are synthesized by solid phase peptide synthesis.

This invention provides methods for using scintigraphic imaging agents that are Tc-99m labeled reagents for imaging thrombi within a mammalian body by obtaining in vivo gamma scintigraphic images. These methods comprise administering an effective diagnostic amount of Tc-99m labeled reagents of the invention and detecting the gamma radiation emitted by the Tc-99m label localized at the thrombus site within the mammalian body.

Specific preferred embodiments of the present invention will become evident from the following more detailed description of certain preferred embodiments and the claims.

DETAILED DESCRIPTION OF THE INVENTION

The present invention provides reagents, including peptide reagents, for preparing radiolabeled thrombus imaging agents for imaging a thrombus within a mammalian body. The reagents provided by the invention comprise a radiolabel binding moiety covalently linked to a specific binding compound that binds a platelet receptor that is the platelet GPIIb/IIIa receptor and is capable of inhibiting human platelet aggregation in platelet-rich plasma by 50% when present at a concentration of no more than 0.3 μM. For purposes of the invention, the term thrombus imaging reagent will refer to embodiments of the invention comprising a specific binding compound covalently linked to a radiolabel-complexing moiety and radiolabeled, preferably with Tc-99m, $^{111}$In or $^{68}$Ga, most preferably with Tc-99m.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Another advantage of the present invention is that none of the preferred radionuclides are toxic, in contrast to other radionuclides known in the art (for example, $^{125}$I).

In the Tc-99m complexing moieties and compounds covalently linked to such moieties that contain a thiol covalently linked to a thiol protecting groups [(pgp)$^s$] provided by the invention, the thiol-protecting groups may be the same or different and may be but are not limited to:

—$CH_2$-aryl (aryl is phenyl or alkyl or alkyloxy substituted phenyl);

—CH-(aryl)$_2$, (aryl is phenyl or alkyl or alkyloxy substituted phenyl);

—C-(aryl)$_3$, (aryl is phenyl or alkyl or alkyloxy substituted phenyl);

—$CH_2$-(4-methoxyphenyl);

—CH-(4-pyridyl)(phenyl)$_2$;

—C($CH_3$)$_3$

—9-phenylfluorenyl;

—$CH_2$NHCOR (R is unsubstituted or substituted alkyl or aryl);

—$CH_2$—NHCOOR (R is unsubstituted or substituted alkyl or aryl);

—CONHR (R is unsubstituted or substituted alkyl or aryl);

—$CH_2$—S—$CH_2$-phenyl

Preferred protecting groups have the formula —$CH_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each specific-binding peptide-containing embodiment of the invention is comprised of a sequence of amino acids. The term amino acid as used in this invention is intended to include all L- and D, primary α- or β-amino acids, naturally occurring and otherwise. Specific-binding peptides provided by the invention include but are not limited to peptides having the following sequences (the amino acids in the following peptides are L-amino acids except where otherwise indicated):

(SEQ ID NO.: 1)

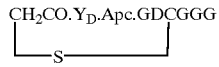

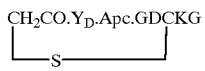
(SEQ ID NO.: 2)

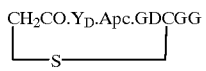
(SEQ ID NO.: 3)

(SEQ ID NO.: 4)

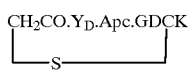
(SEQ ID NO.: 5)

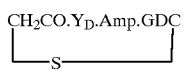
(SEQ ID NO.: 6)

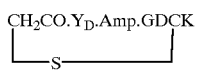
(SEQ ID NO.: 7)

and O-(4-piperdinyl)butyl tyrosine.

Specific-binding peptides of the present invention can be chemically synthesized in vitro. Peptides of the present invention can generally advantageously be prepared on an peptide synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

Radiolabel binding moieties of the invention may be introduced into the target specific peptide during peptide synthesis. For embodiments comprising picolinic acid [(Pic-); e.g., Pic-GlyCys(protecting group)-], the radiolabel-binding moiety can be synthesized as the last (i.e., amino-terminal) residue in the synthesis. In addition, the picolinic acid-containing radiolabel-binding moiety may be covalently linked to the $\epsilon$-amino group of lysine to give, for example, $\alpha$N(Fmoc)-Lys-$\epsilon$N[Pic-Gly-Cys(protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic-Gly-Cys- and -Cys-Gly-Pica chelators are provided in the Examples hereinbelow. This invention provides for the incorporation of these chelators into virtually any peptide capable of specifically binding to a thrombus in vivo, resulting in a radiolabeled peptide having Tc-99m held as neutral complex.

This invention also provides specific-binding small synthetic peptides which incorporate bisamine bisthiol (BAT) chelators which may be labeled with Tc-99m. This invention provides for the incorporation of these chelators into virtually any peptide capable of specifically binding to a thrombus in vivo, resulting in a radiolabeled peptide having Tc-99m held as neutral complex. An example of a small synthetic peptide containing a BAT chelator as radiolabel-binding moiety is provided in the Examples hereinbelow.

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a preformed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts. In a preferred embodiment of the invention, a kit for preparing technetium-labeled peptides is provided. An appropriate amount of the reagent is introduced into a vial containing a reducing agent, such as stannous chloride, in an amount sufficient to label the reagent with Tc-99m. An appropriate amount of a transfer ligand as described (such as tartrate, citrate, gluconate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Radiolabeled thrombus imaging reagents according to the present invention may be prepared by the addition of an appropriate amount of Tc-99m or Tc-99m complex into the vials and reaction under conditions described in Example 4 hereinbelow.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

The thrombus imaging reagents provided by the present invention can be used for visualizing thrombi in a mammalian body when Th-99m labeled. In accordance with this invention, the Tc-99m labeled reagents are administered in a single unit injectable dose. The Tc-99m labeled reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging of the thrombus in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

It will also be recognized by those having skill in the relevant arts that thrombi are commonly found at sites of atherosclerotic plaque; that integrin receptors that may bind to the scintigraphic imaging agents of the invention may be found in certain tumors; and that such integrin receptors are involved in cell adhesion processes that accompany or initiate leukocyte localization at sites of infection. Therefore it will be recognized that the scintigraphic imaging agents of this invention have additional utility as imaging agents for imaging sites in which the GPIIb/IIIa receptor is expressed, including atherosclerotic plaques, tumors and sites of infection.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Synthesis of BAT-BM (N-[2-(N',N'-bis(2-maleimidoethyl)aminoethyl)]-$N^6$,$N^9$-bis(2-methyl-2-triphenylmethylthiopropl)-6,9-diazanonanamide)

BAT-BM was prepared as follows. BAT acid ($N^9$-(t-butoxycarbonyl)-$N^6$,$N^9$-bis(2-methyl-2-triphenylmethylthiopropyl)-6,9-diazanonanoicacid)(10.03 g, 10.89 mmol) and 75 mL of dry methylene chloride ($CH_2Cl_2$) were added to a 250 mL round-bottomed flask equipped with magnetic stir bar and argon balloon. To this solution was added diisopropyl carhodiide (3.40 mL, 21.7 mmol, 199 mole %), followed by N-hydroxy-succinimide (3.12 g, 27.1 mmol, 249 mole %). This solution was observed to become cloudy within 1 h, and was further incubated with stirring for a total of 4 h at room temperature. A solution of tris(2-aminoethyl)amine (30 mL, 200 mmol, 1840 mole %) in 30 mL methylene chloride was then added and stirring continued overnight. The reaction mixture was then concentrated under reduced pressure, and the residue partitioned between ethylacetate (150 mL) and 0.5 M potassium carbonate ($K_2CO_3$; 150 mL). The organic layer was separated, washed with brine and concentrated to give the crude product N-[2-(N',N'-bis(2-aminoethyl)amino ethyl)]-$N^9$-(t-butoxycarbonyl)-$N^6$,$N^9$-bis(2-methyl-2-triphenylmethylthiopropyl-6,9-diazanonanamide as a foam/oil.

This crude product was added to a 1000 mL round-bottomed flask, equipped with magnetic stir bar, containing 300 mL THF, and then 30 mL saturated sodium bicarbonate ($NaHCO_3$), 100 mL water and N-methoxycarbonyl maleimide (6.13 g, 39.5 mmol, 363 mole %) were added. This heterogeneous mixture was stirred overnight at room temperature. THF was removed from the mixture by rotary evaporation, and the aqueous residue was twice extracted with ethylacetate (2×75 mL). The combined organic layers of these extractions were washed with brine, dried over sodium sulfate, filtered through a medium frit and concentrated to about 12 g of crude product. Purification by liquid chromatography (250 g silicon dioxide/eluted with a gradient of chloroform→2% methanol in chloroform) afforded 5.3 g of pure product (N-[2-(N',N'-bis(2-maleimidoethyl) aminoethyl)]-$N^9$-(t-butoxycarbonyl)-$N^6$,$N^9$-bis(2-methyl-2-triphenylmethylthiopropyl)-6,9-diazanonanamide) (equivalent to 40% yield), along with approximately 5 g of crude product that can be repurified to yield pure product. Chemical analysis of the purified product confirmed its identity as BAT-BM as follows:

$^1$H NMR (200 mHz, $CDCl_3$): δ0.91 (12H,s), 1.38 (9H,s), 1.2–1.6 (4H,m), 2.06 (2H,s), 2.18 (2H,t,J=7), 2.31 (4H,m), 2.55 (2H,t,J=5), 2.61 (4H,t,J=6), 2.99 (2H,s), 3.0–3.3 (4H, m), 3.46 (4H,t,J=6), 6.49 (—NH,t,J=4), 6.64 (4H,s), 7.1–7.3 (18H,m), 7.6 (12H,t,J=17).

EXAMPLE 2

Synthesis of TMEA [tris(2-maleimidoethyl)amine]

tris(2-aminoethyl)amine (1.49 mL, 10 mmol) dissolved in 50 mL saturated aqueous sodium bicarbonate and cooled in an ice bath, was treated with N-carbomethoxymaleimide (4.808 g, 31 mmol). The mixture was stirred for 30 min on ice and then for another 30 min at room temperature. The mixture was then partitioned between dichloromethane and water, dried over magnesium sulfate, filtered and evaporated to give 3.442 g of product. Reverse phase thin-layer chromatography (RP-TLC) yielded essentially 1 spot ($R_f$=0.63 in 1:1 acetonitrile:0.5 M sodium chloride). 3.94 mmol (1.817 g) of this product was dissolved in 20 mL tetrahydrofuran and 20 mL saturated sodium bicarbonate and mixed for 2 h. The reaction mixture was then partitioned between ethyl acetate and water. The organic phase was washed with saturated sodium chloride, dried over magnesium sulfate, and filtered. The ethyl acetate solution was diluted with hexanes and cooled. Solid TMEA was collected by filtration and dried to a yield of 832 mg. Chemical analysis of the product confirmed its identity as TMEA as follows:

$^1$H NMR ($CDCl_3$): 2.65 (tr. 2H), 3.45 (tr.2H). 6.64 (s. 2H). $^{13}$C NMR ($CDCl_3$), 35.5, 51.5, 133.9, 170.4.

EXAMPLE 3

Synthesis of tris[2-(2-chloroacetamido)ethyl]amine tris[2-(2-chloroacetamido)ethyl]amine was prepared as follows. To a solution of tris(2-aminoethyl)amine (1.49 mL, 10 mmol) in dichloromethane (50 mL) was added powdered $K_2CO_3$ (6.9 g, 50 mmol) followed by chloroacetyl chloride (2.6 mL, 33 mmol) dropwise. Vigorous boiling resulted. The mixture was cooled and 50 mL water added. The organic layer was separated, dried over $MgSO_4$ and evaporated to give the title compound as a crystalline solid (2.5 g, 6.6 mmol, equal to 66% yield). Thin layer chromatography, performed using C18 reverse phase chromatography plates and a 50:50 mixture of acetonitrile and 0.5 M NaCl in water, showed a single spot with $R_f$ equal to 0.62. The melting point of the crystals of the title compound so produced was determined to be between 116–119° C.

EXAMPLE 4

Synthesis of 1,2-bis2-(2-chloroacetamido) ethoxylethane 1,2-bis[2-(2-chloroacetamido)ethoxy]ethane was prepared as follows. To a mixture of 1,2-bis(2-aminoethoxy) ethane (1.5 g, 10 mmol) in dichloromethane (100 mL) and 1 M $Na_2CO_3$ (50 mL) cooled in an ice bath was added chloroacetyl chloride (2.6mL, 33 mmol) dropwise. After stirring for 10 minutes, the organic layer was separated and evaporated to give the title compound (2.6 g, eual to 92% yield). HLPC analysis revealed a single peak using ultraviolet (220 nm) absorbtion spectrometry.

EXAMPLE 5

Synthesis of Nε-(Nα,Nε-bis-chloroacetyllysyl)lysyl-glycyl-(S-trityl)cysteinamide Nε-(Nα,Nε-bis-chloroacetyllysyl)lysyl-glycyl-(S-trityl) cysteinamide was prepared as follows. The protected peptide was synthesized using SPPS methodology as described in Example 7 using Rink amide resin, (Fmoc)Cys(Trt), (Fmoc)Gly, (Boc)Lys(Fmoc), (Fmoc)Lys(Fmoc) and chloroacetic acid. The peptide was cleaved from the resin, deprotected and re-S-tritylated to give the title compound which was then purified by reverse phase HPLC. Synthesis was confirmed using FABMS; MH$^+$ was found to be 828 and 830 for a peptide having a theoretical molecular weight of 829 (average).

EXAMPLE 6

Synthesis of Nα-(Fmoc)-4-(N-pentamethylchromansulfonyl)amidino phenylalanine [Fmoc-Amp(Pmc)]

Title compound Fmoc-Amp(Pmc) was prepared as follows. D,L-acetyl-4-cyanophenylalanine was prepared from α-bromotoluonitrile and diethyl acetamidomalonate using conventional techniques (see Marvel, 1955, *Org. Syn. Cell.* 3: 705–708) and resolved by selective hydrolysis of the L-epimer using hog renal acylase (see Greenstein et al., 1961, in *Chemistry of the Amino Acids,* Kreiger & Malabar, eds., pp. 2172–2174).

L-4-cyanophenylalanine was converted to the N-α-Boc, t-butyl ester using conventional techniques. The N-α-Boc-4-cyanophenylalanine, t-butyl ester was converted into the 4-amidino derivative using the method of Voigt et al. (1988, *Pharmazie* 43: 412–414). The resulting N-α-Boc4-amidinophenylalanine, t-butyl ester was converted into the N-amidinopentamethylchromansulfonyl (Pmc) derivative essentially as described for arginine (see Ramage et al., 1987, *Tetrahedron Lett.* 28: 2287–2290). The Boc and t-butyl groups were then removed using BF$_3$.OEt/acetic acid. The resulting 4-pentamethylchromasulfonyl-amidinophenylalanine was converted to the title compound using N-(fluorenylmethoxycarboxy)succinimide (FmocOSu).

The title compound was analyzed by HPLC and found to have a retention time of 10.4 minutes using a waters Nova-Pak C18 reverse phase radial compression column and eluted at 3 mL/min with a gradient of 100% (0.1% TFA/water) to 100% (0.1% TFA/10% water/acetonitrile) over 10 minutes. The title compound was analyzed by $^1$H NMR spectrometry and found to have the following $^1$H NMR spectrum (sample dissolved in CDCl$_3$): δ1.25 (s, 6H), 1.72 (t, 2H), 2.1 (s, 3H), 2.55 (m, 8H), 3.1 (m, 2H), 4.05–4.7 (m, 4H), 5.5 (d, 1H) and 7.0–8.0 (m, 15H).

EXAMPLE 7

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotmazole or 2-(1H-benzotriazol-1-yl)-1,1,3,3-tetramethyluronium hexafluorophosphate/hydroxybenzotriazole (HBTU/HOBT), and using p-hydroxymethylphenoxymethyl-polystyrene (HMP) resin for carboxyl-terminus acids or Rink amide resin for carboxyl-terminus amides. Resin-bound products were routinely cleaved using a solution comprised of trifluoroacetic acid or 50/50 trifluoroacetic acid/dichloromethane, optionally containing water, thioanisole, ethanedithiol, and triethylsilane, prepared in ratios of 100:5:5:2.5:2 for 1.5–3 h at room temperature.

Where appropriate, N-terminal acetyl groups were introduced by treating the free N-terminal amino peptide bound to the resin with 20% v/v acetic anhydride in NMP (N-methylpyrrolidinone) for 30 min. For preparing branched-chain peptide reagents involving peptide chain synthesis from both the α- and ε-amines of lysine, Nα(Fmoc)Nε(Fmoc)-lysine was used during SPPS. Where appropriate, 2-chloroacetyl and 2-bromoacetyl groups were introduced either by using the appropriate 2-halo-acetic acid as the last residue to be coupled during SPPS or by treating the N-terminus free amino peptide bound to the resin with either the 2-halo-acetic acid/diisopropylcarbodiimide/N-hydroxysuccinimide in NMP of the 2-halo-acetic anhydride/diisopropylethylamine in NMP. Where appropriate, HPLC-purified 2-haloacetylated peptides were cyclized by stirring in a 0.1–1.0 mg/mL solution at pH8 optionally containing phosphate, bicarbonate or 0.5–1.0 mM EDTA for 0.5–48 hours, followed by acidification with acetic acid, lyophilization and HPLC purification. Where appropriate, Cys-Cys disulfide bond cyclizations were performed by treating the precursor cysteine-free thiol peptides at 0.1 mg/mL in pH 7 buffer with aliquots of 0.006 M K$_3$Fe(CN)$_6$ until a stable yellow color persisted. The excess oxidant was reduced with excess cysteine, the mixture was lyophilized and then purified by HPLC.

Where appropriate, peptide thiol-chloroacetyl derived sulfides were prepared by reacting single thiol-containing peptides at a concentration of 2 to 50 mg/mL in water and acetonitrile or THF or DMF at pH 10 with the appropriate number (e.g., 0.5 molar equivalents for preparing dimers and 0.33 molar equivalents for preparing trimers) of the chloroacetyl polyvalent linker moiety for 0.5 to 24 hours. The solution was then neutralized with acetic acid, evaporated to dryness, and, if necessary, deprotected using 10 mL TFA and scavengers such as 0.2 mL triethylsilane for 30 to 90 minutes. The solution was concentrated and the product was precipitated with ether. Products were purified by preparative HPLC.

Where appropriate, BSME adducts were prepared by reacting single thiol-containing peptides (5 to 50 mg/mL in 50 mM sodium phosphate buffer, pH 7 to 8) with 0.5 molar equivalents of BMME (bis-maleimidomethylether) pre-dissolved in acetonitrile at room temperature for approximately 1–18 hours. The solution was concentrated and the product was purified by HPLC.

Where appropriate, TSEA adducts were prepared by reacting single thiol-containing peptide (at concentrations of 10 to 100 mg/mL peptide in DMF, or 5 to 50 mg/mL peptide in 50 mM sodium phosphate (pH 8)/acetonitrile or THF) with 0.33 molar equivalents of TMEA (tris(2-maleimidoethyl)amine; Example 2) pre-dissolved in acetonitrile or DMF, with or without 1 molar equivalent of triethanolamine, at room temperature for approximately 1–18 h. Such reaction mixtures containing adducts were concentrated and the adducts were then purified using HPLC.

Where appropriate, BAT-BS adducts were prepared by reacting single thiol-containing peptide (at concentrations of 2 to 50 mg/mL peptide in 50 mM sodium phosphate (pH 8)/acetonitrile or THF) with 0.5 molar equivalents of BAT-BM (N-[2-(N',N'-bis(2-maleimidoethyl)aminoethyl)]-$N^9$-(t-butoxycarbonyl)-$N^6$,$N^9$-bis(2-methyl-2-triphenylmethylthiopropyl)-6,9-diazanonanamide; Example 1) pre-dissolved in acetonitrile or THF, at room temperature for approximately 1–18h. The solution was then evaporated to dryness and [BAT-BS]-peptide conjugates deprotected by treatment with 10 mL TFA and 0.2 mL triethylsilane for 1 h. The solution was concentrated, the product adducts precipitated with ether, and then purified by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS) or electrospray mass spectroscopy (ESMS).

EXAMPLE 8

A General Method for Radiolabeling with Tc-99m 0.1 mg of a peptide prepared as in Example 2 was dissolved in 0.1 mL of water or 50 mM potassium phosphate buffer, 0.1 M bicarbonate buffer or 10% hydroxypropylcyclodextrin (HPCD), each buffer at pH of 5–10. Tc-99m gluceptate was prepared by reconstituting a Glucoscan vial (E. I. DuPont de Nemours, Inc.) with 1.0 mL of Tc-99m sodium pertechnetate containing up to 200 mCi and allowed to stand for 15 minutes at room temperature. 25 $\mu$l of Tc-99m gluceptate was then added to the peptide and the reaction allowed to proceed at room temperature or at 100° C. for 15–30 min and then filtered through a 0.2 $\mu$m filter.

The Tc-99m labeled peptide purity was determined by HPLC using the following conditions: a Waters DeltaPure RP-18, 5$\mu$, 150 mm×3.9 mm analytical column was loaded with each radiolabeled peptide and the peptides eluted at a solvent flow rate equal to 1 mL/min. Gradient elution was performed beginning with 10% solvent A (0.1% CF3COOH/$H_2O$) to 40% solvent $B_{90}$ (0.1% $CF_3COOH$/90% $CH_3CN$/$H_2O$) over the course of 20 min.

The Tc-99m labeled peptide purity was determined by HPLC using the conditions described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 1 using the method described herein.

TABLE I

| Peptides | FABMS $MH^+$ | Radiochemical Yield (%)* | HPLC $R_T$ (min)** |
|---|---|---|---|
| CH$_2$CO.Y$_D$RGDCC$_{Acm}$GC$_{Acm}$amide$^b$ (SEQ ID NO.: 8) | 1057 | 97$^2$ | 10.0, 10.4, 10.6$^2$ |
| CH$_2$CO.Y$_D$RGDCGGC$_{Acm}$GC$_{Acm}$amide (SEQ ID NO.: 9) | 1171 | 99$^2$ | 13.5$^2$ |
| CH$_2$CO.Y$_D$.Apc.GDCGGGC$_{Acm}$GC$_{Acm}$amide (SEQ ID NO.: 10) | 1233 | 100$^4$ | 17.1, 18.1$^2$ |
| GRGDVRGDFKC$_{Acm}$GC$_{Acm}$amide (SEQ ID NO.: 11) | 1510 | 97$^2$ | 16.2, 16.8$^2$ |
| GRGDVRGDFC$_{Acm}$GC$_{Acm}$amide (SEQ ID NO.: 12) | 1382 | 94$^2$ | 16.4$^2$ |
| CH$_2$CO.Y$_D$Apc.GDCGGC$_{Acm}$GC$_{Acm}$GGF$_D$PRPG.NH$_2$ (SEQ ID NO.: 13) | 1845 | 90$^4$ | 16.6, 16.9$^2$ |
| (CH$_2$CO.Y$_D$Apc.GDCGGC$_{Acm}$GC$_{Acm}$GGC.amide)$_2$-BSME | 3020$^a$ | 98$^4$ | 9.3$^2$ |
| (CH$_2$CO.Y$_D$.Apc.GDCggc$_{Acm}$GC$_{Acm}$GGC.amide)$_3$-TSEA | 4596 | 99$^4$ | 9.2, 11.6$^5$ |
| (CH$_2$CO.Y$_D$Apc.GDCGGC$_{Acm}$GC$_{Acm}$GGC.amide)$_2$-[BAT-BS] | 3409$^a$ | 98$^3$ | 10.3$^5$ |
| C$_{Acm}$GC$_{Acm}$RRRRRRRRRGDV (SEQ ID NO.: 14) | 2100 | 100$^2$ | 2.4$^{3***}$ |
| (CH$_2$CO.Y$_D$Apc.GDCKGC$_{Acm}$GC$_{Acm}$GGC.amide)$_2$-BSME | 3163$^a$ | 98$^4$ | 9.6$^5$ |
| (CH$_2$COY$_D$.Apc.GDCGGC$_{Acm}$GC$_{Acm}$GGCamide)$_2$-K(Nε-K)GCamide | 3298$^a$ | 96$^3$ | 12.0$^4$ |
| (CH$_2$COY$_D$.Amp.GDCGGC$_{Acm}$GC$_{Acm}$GGCamide)$_2$-(CH$_2$CO)$_2$K(Nε-K)GCamide | 3357$^a$ | 99$^8$ | 4.6$^6$ |
| (CH$_2$COY$_D$.Amp.GDCKGCGamide)$_2$-(CH$_2$CO)$_2$K(Nε-K)GCamide | 2573$^a$ | 98$^8$ | 4.8$^6$ |

*Superscripts refer to the following labeling conditions:
$^1$The peptide was dissolved in 50 mM potassium phosphate buffer (pH 7.4) and labeled at room temperature.
$^2$The peptide was dissolved in 50 mM potassium phosphate buffer (pH 7.4) and labeled at 100° C.
$^3$The peptide was dissolved in water and labeled at room temperature.
$^4$The peptide was dissolved in water and labeled at 100° C.
$^5$The peptide was dissolved in 50 mM potassium phosphate buffer (pH 6.0) and labeled at 100° C.
$^6$The peptide was dissolved in 50 mM potassium phosphate buffer (pH 5.0) and labeled at room temperature.
$^7$The peptide was dissolved in 50:50 mixture of ethanol/water and labeled at 100° C.
$^8$The peptide was dissolved in 0.9% sodium chloride solution and labeled at room temperature.
**HPLC methods (indicated by superscript after $R_T$):

TABLE I-continued

| Peptides | FABMS MH+ | Radiochemical Yield (%)* | HPLC $R_T$ (min)** |
|---|---|---|---| general:
solvent A =0.1% CF$_3$COOH/H$_2$O
solvent B$_{70}$ =0.1% CF$_3$COOH/70% CH$_3$CN/H$_2$O
solvent B$_{90}$ =0.1% CF$_3$COOH/90% CH$_3$CN/H$_2$O
sovent flow rate =1 mL/min
Vydak column =Vydak 218TP54 RP-18, 5 vm, 220 mm x 4.6 mm analytical column with guard column
Brownlee column =Brownlee Spheri-5 RP-18, 5 μm, 220 mm x 4.6 mm column
Waters column =Waters Delta-Pak C18, 5μm, 150 mm x 3.9 mm column
Waters column 2 =Waters Nova-Pak C18, 5μm, 100 mm x 8 mm radial compression column
Method 1: Brownlee column 100% A to 100% B$_{70}$ in 10 min
Method 2: Vydak column 100% A to 100% B$_{90}$ in 10 min
Method 3: Vydak column 100% A to 100% B$_{70}$ in 10 min
Method 4: Waters column 100% A to 100% B$_{90}$ in 20 min
Method 5: Waters column 100% A to 100% B$_{90}$ in 10 min
Method 6: Waters 2 column 100% A to 100% B$_{90}$ in 10 min
***Confirmed by sodium dodecyl sulfate-polyacrylamide gel electrophoresis
Single-letter abbreviations for amino acids can be found in G. Zubay, Biochemistry (2d. ed.), 1988
(MacMillen Publishing: New York) p.33; underlining indicates the formation of a thiol linkage between the
linked amino acids of derivative groups; peptides are linked to BSH, ETAC, BSME, TSEA, [BAT-BS] OR
(CH$_2$CO)-containing linkers via the free thiol moiety of the unprotected cysteine residue (C) in each pep-
tide;
Ac = acetyl;
Bz = benzoyl;
Pic = picolinoyl (pyridine-2-carbonyl);
Acm = acetamidomethyl;
Mob = 4-methoxybenzyl;
Apc = L-[S-(3-aminopropyl)cysteine;
Hly = homolysine;
F$_D$ = D-phenylalanine;
Y$_D$ = D-tyrosine;
ma = 2-mercaptoacetic acid;
mmp = 2-mercapto-2-methylpropionic acid;
BAT = N$^6$,N$^9$-bis(2-mercapto-2-methylpropyl)-6,9-diazanonanoic acid;
ETAC = 4-(O-CH$_2$CO-Gly-Gly-Cys.amide)acetophenone;
BAT-BS = N-[2-N',N'-bis(2-succinimidoethyl)aminoethyl]-N$^6$,N$^9$-bis(2-mercapto-2-methylpropyl)-6,9-
diazanonanamide;
BSME = bis-succinimidomethylether;
TSEA = tris-(2-succinimidoethyl)amine;
NES = N-ethylsuccinimide;
BSH = 1,6-bis-succinimidohexane;
Amp = 4-amidinophenylalanine
[a]confirmed by electrospray mass spectrometry [ESMS]

EXAMPLE 9

Platelet Aggregation Inhibition Assays

Platelet aggregation studies were performed essentially as described by Zucker (1989, Methods in Enzymol. 169: 117–133). Briefly, platelet aggregation was assayed with or without putative platelet aggregation inhibitory compounds using fresh human platelet-rich plasma, comprising 300,000 platelets per microliter. Platelet aggregation was induced by the addition of a solution of adenosine diphosphate to a final concentration of 10 to 15 micromolar, and the extent of platelet aggregation monitored using a Bio/Data aggregometer (Bio/Data Corp., Horsham, Pa.). The concentrations of platelet aggregation inhibitory compounds used were varied from 0.1 to 500 μg/mL. The concentration of inhibitor that reduced the extent of platelet aggregation by 50% (defined as the IC$_{50}$) was determined from plots of inhibitor concentration versus extent of platelet aggregation. An inhibition curve for peptide RGDS was determined for each batch of platelets tested.

The results of these experiments are shown in Table II. In Table II, the compounds tested are as follows (RGDS is given as a positive control):

P47=AcSYGRGDVRGDFKC$_{Acm}$GC$_{ACm}$ (SEQ ID NO.:15)

P97=GRGDVRGDFKC$_{Acm}$GC$_{Acm}$amide (SEQ ID NO.:11)

P32=C$_{Acm}$GC$_{Acm}$RRRRRRRRRGDV (SEQ ID NO.:14)

P143=CH$_2$CO-Y$_D$RGDCGGC$_{Acm}$GC$_{Acm}$amide (SEQ ID NO.:9)

P245=CH$_2$CO-Y$_D$,Apc, AGDCGGC$_{Acm}$GC$_{Acm}$GGF$_D$PRPGamide (SEQ ID NO.:13)

P63=AcSYGRGDVRGDFKCTCCA (SEQ ID NO.:16)

P98=GRDGVRGDFC$_{Acm}$GC$_{Acm}$amide (SEQ ID NO.:12)

P81=CH$_2$CO-Y$_D$RGDCC$_{Acm}$GC$_{Acm}$amide (SEQ ID NO.:8)

P154=CH$_2$CO-Y$_D$ApcGDGGGC$_{Acm}$GC$_{Acm}$amide (SEQ ID NO.:10)

P381 = (CH₂CO—Y_DApcGDCKGC_AcmGC_AcmGGC-amide)₂-BSME
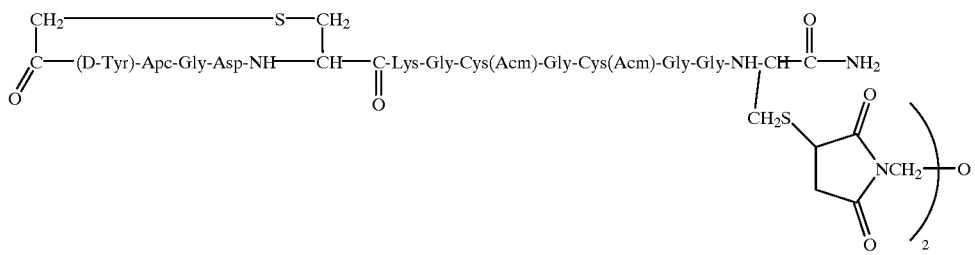
P317 = (CH₂CO—Y_DApcGDCGGC_AcmGC_AcmGGC-amide)₂-TSEA
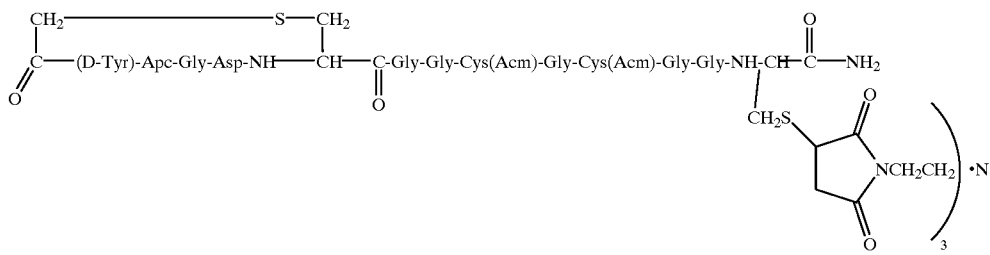
P280 = (CH₂CO—Y_DApcGDCGGC_AcmGC_AcmGGC-amide)₂-BSME
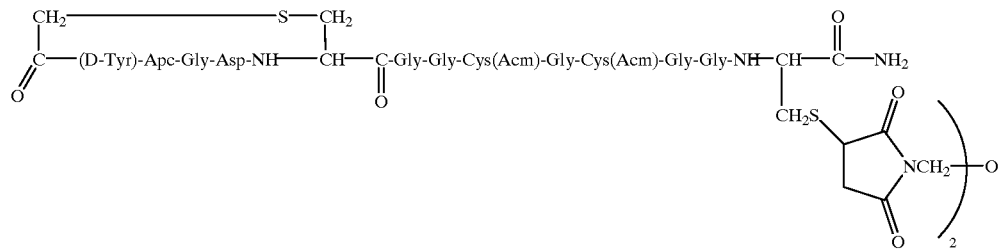
P357 = (CH₂CO—Y_DApcGDCGGC_AcmGC_AcmGGC-amide)₂-[BAT-BS]
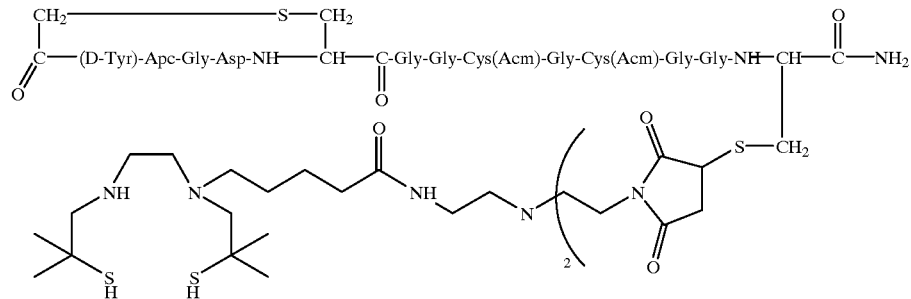
P667 = (CH₂COY_D, Apc, GDCGGC_ACMGC_ACMGGC_amide)₂(CH₂CO)₂K(Nε-K)GCamide
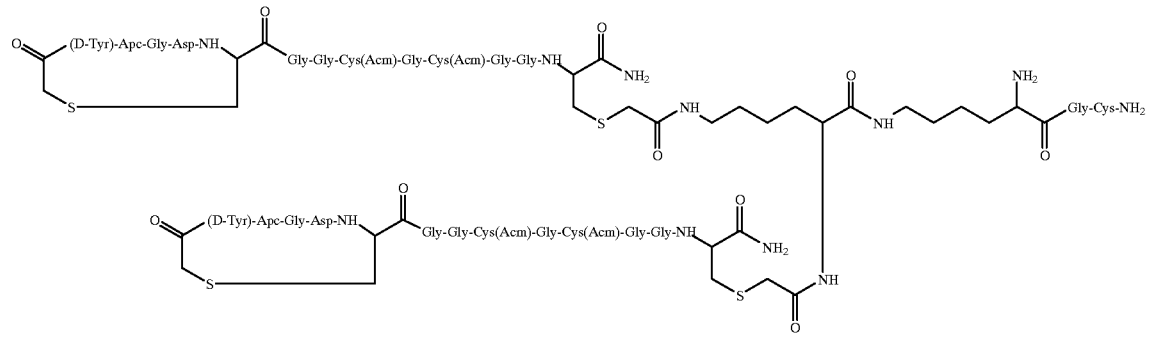

-continued

P747 = (CH$_2$COY$_D$, Amp, GDCGGC$_{Acm}$GC$_{Acm}$GGC$_{amide}$)$_2$(CH$_2$CO)$_2$K(Nε-K)GCamide

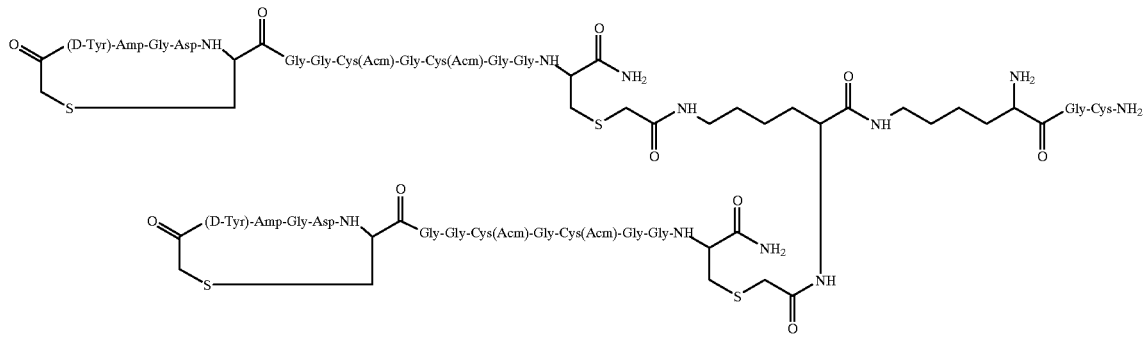

P748 = (CH$_2$COY$_D$, Amp, GDCKGCC$_{amide}$)$_2$(CH$_2$CO)$_2$K(Nε-K)GCamide

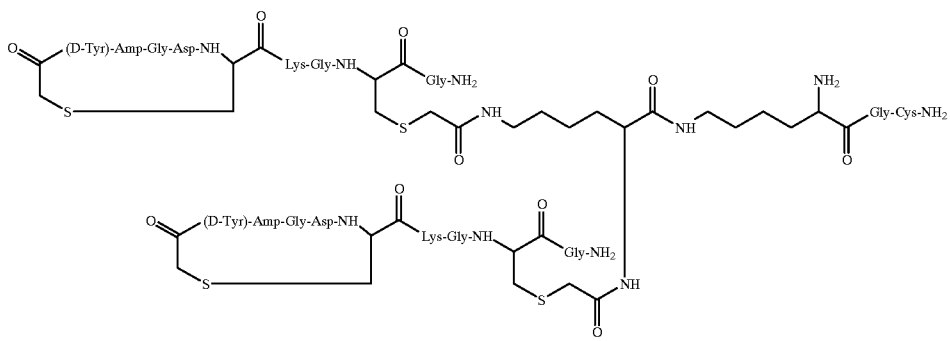

(Single-letter abbreviations for amino acids can be found in G. Zubay, Biochemistry (2d. ed.), 1988 (MacMillen Publishing: New York) p.33; Ac = acetyl;
Acm = acetamidomethyl; Apc = L-[S-(3-aminopropyl)cysteine; Y$_D$ = D-tyrosine; BSME = bis-succinimidylmethylether; TSEA = tris(succinimidylethyl)amine;
[BAT-BS] = N-[2-(N', N'-bis(2-succinimidoethyl)aminoethyl)]-N$^6$, N$^9$, -bis(2-methyl-2-mercaptopropyl)-6, 9-diazanonanamide;
peptides are linked to BSME, TSEA, [BAT-BS] or (CH$_2$CO)-containing linkers via the free thiol moiety of the unprotected cysteine reside (C) in each peptide).

These results demonstrate that the IC$_{50}$ decreases for cyclic peptides as compared with linear ones, and is even less for polyvalent peptide agents as compared with monovalent peptide agents. These results illustrate the efficacy of the multimeric polyvalent antithrombotic agents of the invention at reducing platelet aggregation.

TABLE II

| Peptides | IC$_{50}$(μM)** | Clot/Blood* |
|---|---|---|
| P357 | 0.079 | 6.3 ± 3.4[6] |
| P667 | 0.081 | 5.9, 5.0[2] |
| P280 | 0.090 | 4.4 ± 1.8[5] |
| P682 | 0.130 | 4.0[1] |
| P317 | 0.036 | 3.8 ± 2.2[3] |
| P381 | 0.035 | 2.5 |
| P154 | 0.3 | 2.0 ± 0.5[3] |
| P245 | 0.5 | 1.5 |
| P143 | 1.3 | 1.4 |
| P97 | 8 | 1.0 |
| P98 | 15 | 1.7 |
| P63 | 19 | 1.7 |
| P47 | 23 | 1.0 |

TABLE II-continued

| Peptides | IC$_{50}$(μM)** | Clot/Blood* |
|---|---|---|
| P81 | 25 | 1.8 ± 0.6[3] |
| P32 | 26 | 1.2 ± 0.2[4] |

[1]n = 1;
[2]n = 2;
[2]n = 3;
[4]n = 4;
[5]n = 6;
[6]n = 9
*ratio of (% injected dose/g in a femoral vein thrombus)/(% injected dose/g in blood) at approximately 4 h post-injection of each Tc-99 m labeled reagent in a canine model of DVT
**concentration of reagent that inhibits by 50% the aggregation of human platelets in platelet-rich plasma induced to aggregate by the addition of adenosine diphosphate (ADP)

It should be understood that the foregoing disclosure emphasizes certain specific embodiments of the invention and that all modifications or alternatives equivalent thereto are within the spirit and scope of the invention as set forth in the appended claims.

What is claimed is:

1. A reagent for preparing a thrombus imaging agent comprising, in combination, a technetium-99m complexing moiety covalently linked to a platelet glycoprotein IIb/IIIa receptor binding moiety having a molecular weight of less than 10,000 daltons, wherein the reagent inhibits human platelet aggregation in platelet-rich plasma by 50% ($IC_{50}$) when the reagent is present at a concentration of no more than 0.3 μM.

2. The reagent of claim 1, wherein the receptor binding moiety is a peptide comprising from 4 to 100 amino acids.

3. The reagent of claim 1, wherein the technetium-99m complexing moiety has a formula selected from the group consisting of:

$$Cp(aa)Cp$$

wherein Cp is a protected cysteine and (aa) is any primary α- or β-amino acid not containing a thiol group;

[III.]

pyridine—CO-(amino acid)-cysteine—CO—
                              |
                              SX wherein X=H or a protecting group;
    (amino acid)=any primary α- or β-amino acid not containing a thiol group;

[IV.]

—HN-cysteine-(amino acid)—HN—CH$_2$—pyridine
      |
      SX wherein X=H or a protecting group;

(amino acid)=any primary α- or β-amino acid not containing a thiol group;

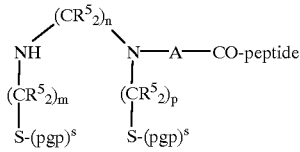

[V.]

wherein each $R^5$ is independently H, $CH_3$ or $C_2H_5$;

each $(pgp)^s$ is independently a thiol protecting group or H;

m, n and p are independently 2 or 3;

A=linear lower alkyl, cyclic lower alkyl, aryl, heterocyclyl, or a combination thereof; and

[VI.]

wherein each $R^5$ is independently H, lower alkyl having 1 to 6 carbon atoms, phenyl, or phenyl substituted with lower alkyl or lower alkoxy;

m, n and p are independently 1 or 2;

A=linear lower alkyl, cyclic lower alkyl, aryl, heterocyclyl, or a combination thereof;

V=H or —CO-peptide;

$R^6$=H or peptide;

and wherein when V=H, $R^6$=peptide and when $R^6$=H, V=—CO-peptide.

4. The reagent of claim 2, wherein the peptide and the technetium-99m complexing moiety are covalently linked through one or more amino acids.

5. The reagent of claim 3, wherein the technetium-99m complexing moiety has the formula

and Cp comprises a protecting group having a formula

wherein R is a lower alkyl having 1 to 6 carbon atoms, 2-pyridyl, 3-pyridyl, 4-pyridyl, phenyl, or phenyl substituted with lower alkyl, hydroxy, lower alkoxy, carboxy, or lower alkoxycarbonyl.

6. The reagent of claim 3, wherein the technetium-99m complexing moiety has the formula:

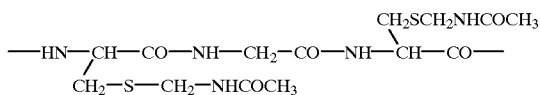

7. A scintigraphic imaging agent comprising the reagent of claim 1, wherein the technetium-99m complexing moiety is complexed with technetium-99m.

8. The reagent of claim 2, wherein the peptide is selected from the group consisting of:

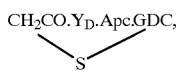
(SEQ ID NO.: 3)

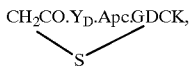
(SEQ ID NO.: 4)

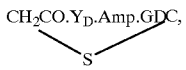
(SEQ ID NO.: 5)

and

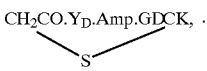
(SEQ ID NO.: 6)

9. A complex formed by reacting the reagent of claim 1 with technetium-99m in the presence of a reducing agent.

10. The complex of claim 9, wherein the reducing agent is selected from the group consisting of a dithionite ion, a stannous ion, and a ferrous ion.

11. A kit for preparing a radiopharmaceutical preparation, said kit comprising a sealed vial containing a predetermined quantity of the reagent of claim 1 and a sufficient amount of a reducing agent to label the reagent with technetium-99m.

12. A process of preparing the reagent of claim 2 by chemical in vitro synthesis.

13. The process of claim 12, wherein the synthesis is solid phase peptide synthesis.

14. A method of labeling the reagent of claim 1, comprising the step of reacting the reagent with technetium-99m in the presence of a reducing agent.

15. The method of claim 14, wherein the reducing agent is selected from the group consisting of a dithionite ion, a stannous ion, and a ferrous ion.

16. The reagent of claim 2, wherein the peptide comprises a cyclic domain having a formula:

$$\text{CR}_2\text{CO}-\text{A}-\text{X-Gly-Asp-Cys}$$
$$\diagdown_S\diagup$$

wherein A is a lipophilic D-α-amino acid, an N-alkyl-L-α-amino acid or L-proline;

X is an L-α-amino acid having a positively charged sidechain; and

R is each independently H, lower alkyl or lower alkoxyalkyl.

17. The reagent of claim 16, wherein A is D-tyrosine or D-phenylalanine and X is L-{S-(3-aminopropyl)cysteine} or L-4-amidinophenylalanine.

18. The reagent of claim 1, wherein the technetium-99m complexing moiety comprises a single thiol-containing moiety of formula:

$$\text{A-CZ(B)-}\{\text{C}(R^1R^2)\}_n\text{-X} \qquad \text{II.}$$

wherein A is H, HOOC, H$_2$NOC, (amino acid or peptide)-NHOC, (amino acid or peptide)-OOC or R$^4$;

B is H, SH, —NHR$^3$, —N($^3$)-(amino acid or peptide), or R$^4$;

X is H, SH, —NHR$^3$, —N(R$^3$)-(amino acid or peptide) or R$^4$;

Z is H or R$^4$;

R$^1$, R$^2$, R$^3$ and R$^4$ are independently H, lower straight chain alkyl, lower branched chain alkyl, or cyclic alkyl;

n is 0, 1, or 2;

and where B is —NHR$^3$ or —N(R$^3$)-(amino acid or peptide), X is SH, and n is 1 or 2;

where Z is methyl, X is methyl, A is HOOC, H$_2$NOC, (amino acid or peptide)-NHOC, (amino acid or peptide)-OOC, B is SH and n is 0;

and wherein (amino acid) is any primary α- or β-amino acid not containing a thiol group.

19. The reagent of claim 18, wherein the technetium-99m complexing moiety is selected from the group consisting of:

-(amino acid)$^1$-(amino acid)$^2$-{A-CZ(B)-(C(R$^1$R$^2$))$_n$-X},

-{ A-CZ(B)-(C(R$^1$R$^2$))$_n$-X}-(amino acid)$^1$-(amino acid)$^2$,

-(a primary α,ω- or β,ω-diamino acid)-(amino acid)$^1$-{A-CZ(B)-(C(R$^1$R$^2$))$_n$-X} and -{A-CZ(B)-(C(R$^1$R$^2$))$_n$-X}-(amino acid)$^1$-(a primary α,ω- or β,ω-diamino acid).

20. A reagent for preparing a thrombus imaging agent comprising:
  a) a polyvalent linker;
  b) at least two platelet glycoprotein IIb/IIIa receptor binding compounds, each compound being covalently linked to the linker; and
  c) at least two radiolabel complexing moieties, each moiety being covalently linked to the linker;

said reagent having a molecular weight of less than about 20,000 daltons;

wherein the reagent inhibits human platelet aggregation in platelet-rich plasma by 50% (IC$_{50}$) when the reagent is present at a concentration of no more than 0.3 μM.

21. The reagent of claim 20, wherein the linker is bis-succinimidylmethylether, 4-(2,2-dimethylacetyl)benzoic acid, N-[2-(N',N'bis(2-succinimidoethyl)aminoethyl)]-N$^6$, N$^9$-bis(2-methyl-2-mercaptopropyl)-6,9-diazanonamide, tris(succinimidylethyl)amine, tris(2-chloroacetamidoethyl)amine, or 1,2-bis(2-chloroacetamidoethoxy)ethane.

22. A method of imaging a thrombus within a mammalian body comprising the steps of:
  a) administering an effective diagnostic amount of the agent of claim 7 to said body; and
  b) detecting technetium-99m accumulated at the thrombus.

23. A composition comprising a reagent having a formula:

[Structure: branched reagent containing two (D-Tyr)-Apc-Gly-Asp-NH-...Gly-Gly-Cys(Acm)-Gly-Cys(Acm)-Gly-Gly-NH- arms linked through a lysine-based scaffold ending in -Gly-Cys-NH$_2$]

where X is —NHR$^3$ or —N(R$^3$)-(amino acid or peptide), B is SH, and n is 1 or 2;

where B is H or R$^4$, A is HOOC, H$_2$NOC, (amino acid or peptide)-NHOC, (amino acid or peptide)-OOC, X is SH, and n is 0 or 1;

where A is H or R$^4$, then where B is SH, X is —NHR$^3$ or —N(R$^3$)-(amino acid or peptide) and where X is SH, B is —NHR$^3$ or —N(l$^3$)-(amino acid or peptide);

where X is H or R$^4$, A is HOOC, H$_2$NOC, (amino acid or peptide)-NHOC, (amino acid or peptide)-OOC and B is SH;